United States Patent [19]
Ninkov

[11] Patent Number: 5,990,178
[45] Date of Patent: Nov. 23, 1999

[54] PHARMACEUTICAL COMPOSITIONS SUITABLE FOR USE AGAINST HISTOMONIASIS

[75] Inventor: Dusan Ninkov, Amsterdam, Netherlands

[73] Assignee: Ropapharm B.V., Zaandam, Netherlands

[21] Appl. No.: 09/162,161

[22] Filed: Sep. 29, 1998

[30] Foreign Application Priority Data

Sep. 30, 1997 [EP] European Pat. Off. ............. 97203004

[51] Int. Cl.[6] .......................... A61K 31/05; A61K 35/78
[52] U.S. Cl. ....................................... 514/731; 424/195.1
[58] Field of Search ....................... 514/731; 424/195.1

[56] References Cited

FOREIGN PATENT DOCUMENTS 53-066420   6/1978   Japan .

WO 97/01348   1/1997   WIPO .

OTHER PUBLICATIONS

Abstract 1923, "Carvacrol", The Merck Index and Encyclopedia of Chemicals, Drugs, and Bilogicals, Twelfth Edition, p. 308, 1996.

Abstract 9540, "Thymol", The Merck Index and Encyclopedia of Chemicals, Drugs, and Bilogicals, Twelfth Edition, p. 1604, 1996.

*Primary Examiner*—Phyllis G. Spivack
*Attorney, Agent, or Firm*—Young & Thompson

[57] ABSTRACT

The invention relates to pharmaceutical compositions comprising carvacrol and/or thymol as active agents in the veterinary field. The compositions according to the invention can be used in the treatment of histomoniasis, an infectious disease of poultry, mainly of turkeys, and in treatment against hemoflagellates.

6 Claims, No Drawings

PHARMACEUTICAL COMPOSITIONS SUITABLE FOR USE AGAINST HISTOMONIASIS

DESCRIPTION

1. Field of Invention

The invention relates to pharmaceutical compositions comprising carvacrol and/or thymol as active agents, a process for the preparation of such pharmaceutical compositions as well as their use in the human and veterinary field, e.g. against histomoniasis.

More in particular histomoniasis is an infectious disease of poultry, mainly turkeys, due to *Histomonas meleagridis* with intestinal and hepatic lesions and dark discoloration of the comb ("black-head"). In detail the trophozoites of *Histomonas meleagridis* and resulting lesions are confined to the cecum and liver. The infected cecum is enlarged and the mucosa becomes necrotic consisting of leather-like cheesy material. The parasites lie singly or in small groups in the spaces between the cells. From the mucosa, they can spread to the submucosa and muscle layers and eventually be carried to the liver via the portal blood. The liver has circular areas or necrotic tissue usually resulting in impaired function. Early liver lesions are small in size, spherical and cream-colored while older lesions are large with depressed dark centers and a pale periphery. Clinical signs include drowsiness, weakness, and sulfur-colored droppings. Transmission can be by ingestion of trophozoites or ingestion of *Heterakis gallinae* (nematode) egg containing the trophozoite. In the latter case the flagellated form of the *H.meleagridis* is ingested by the co-habitating *H.gallinarum* nematode. The Histomonas passes through the gut wall of the female worm and penetrates into the ovary. It multiplies in the ovary and invades the oocysts. When embryonated Heterakis eggs are ingested by the susceptible host, the Histomonas escapes into the lumen of the cecum. Young birds usually have an acute form of the histomoniasis disease while older birds may appear sick for several days prior to becoming emaciated. Heaviest losses occur at 3 to 12 weeks of age. Many other species of birds including quail and pea fowl are also susceptible to above infection. A treatment is possible with nitroimidazole as well as the following medicines Dimetriazol and Ronidazol. Separation of species and ages is vital in preventing this disease.

Further, the invention relates to pharmaceutical compositions, suitable against hemoflagellates. These parasites live in the blood, lymph, and tissue spaces and are typically transmitted from one host to another by blood-feeding arthropods. The most important genera are Trypanosoma and Leishmania. Infection in mammalian hosts occurs either through the bite of the infected arthropod (salivarian) or through contamination of the host's mucus membranes or abraded skin by the arthropod's infected feces (stercorarian).

The pharmaceutical compositions according to the invention are also suitable for combating inflammation diseases like pneumonia, nephritis, metritis, artritis, othitis, pharingitis, gastro-enteritis, sepsis caused by Salmonella spp, Pasteurella spp, *E.coli, Vibrio coli* etc. and any other inflammation in the organism of human and/or animals caused by the bacteria species, causing above-mentioned pathological diseases.

2. Problem Related to the Prior Art

The above-defined diseases are well known in the art, together with the relevant medications therefore. However, the prior art medications have been either forbidden on account of for example the presence of bioresidues in the meat of e.g. turkeys, its cancerogenic properties or they have become less active against the harmful microorganisms in question. Especially in the last decade many pathogenic microorganisms like *Salmonella typhimurium* DT 104 have build up considerable resistance to the marketed antibiotic products.

3. Description of the solution of the above-described problem

The primary component(s) to be applied in the compositions according to the invention is thymol (2-hydroxy-1-isopropyl-4-methylbenzene) and/or carvacrol (2-hydroxy-4-isopropyl-1-methylbenzene). Although above active compounds may have a synthetic origin, preferably the active compounds are applied in the form of an oil extracted from any of the plants, selected from the group consisting of *Origanum vulgaris, Thymus vulgaris, Mentha piperita, Thymus serpilum, Saturea hortensis, Saturea montana, Saturea subricata, Carum corticum, Thymus zugus, Ocimum gratisimum, Moranda pungtata, Mosla japanoica* and *Salvia officinalis*.

The pharmaceutical compositions according to the invention may comprise a pharmaceutically acceptable carrier, preferably of natural origin. Representatives of such carriers are generally known in the human and veterinary pharmaceutical field. Examples of such carriers are lactose, honey, laurel, vaselin, paraffin, starch products, calcium carbonate, etc.

The pharmaceutical compositions may have any form suitable for its application, for instance the form of a water-soluble solution and a powder in the case of the treatment of histomoniasis and in the form of an injectable solution in the case of the above-defined inflammations.

The content of active agent in the pharmaceutical compositions according to the invention, which in fact does also depend on its pharmaceutical use, may vary between wide limits. Preferably the active agent in the form of thymol and/or carvacrol is present in an amount of 1–10% by weight, most preferably 2–5% by weight, calculated on the total weight of the pharmaceutical composition.

Further, to the active agent according to the invention also other active substances, preferably of natural origin, can be used. Such substances may have bacteriological, fungicidal, adstrigidic etc. properties.

The way of application of the pharmaceutical compositions according to the invention depends on their form. For instance, the treatment of histomoniasis may be carried out by means of a water soluble solution or powder per oral, whereas the treatment of the above-defined inflammation diseases may be carried out by means of an injectable solution in an intramuscular, subcutaneous, intraperitoneal and/or intravenous way.

Examples of forms of pharmaceutical compositions according to the invention are for instance:

1) Powder form

The following composition in powder form may be used in the treatment of poultry, e.g. turkeys, against histomoniasis.

$CaCO_3$: 20–25 wt. %

Magnesium stearate: 3–5 wt. %

Potato starch: 25–30 wt. %

Dextrose: 45–50 wt. %

Caivacrol and/or Thymol*: 3–4 wt. %

* In this case carvacrol and/or thymol are applied as an etheric oil extracted from the above-mentioned plants: 6–7 wt. %

2) Water soluble solution

The following composition may be used in the treatment of poultry against histomoniasis.

Double distilled water: 4–5 wt. %

Polysorbate: 60–65 wt. %

Monoethylene glycol: 3–35 wt. %

Caivacrol and/or Thymol**: 3–4 wt. %

** In this case carvacrol and/or thymol are applied as an etheric oil extracted from the above-mentioned plants: 6–7 wt. %

3) Injectable solution

The following composition may be used in the treatment of inflammatory diseases like pneumonia etc.

Double distilled water: 40–55 wt. %

Emulgator 686: 2–3 wt. %

Polysorbate: 40–43 wt. %

Carvacrol and/or Thymol***: 1–3 wt. %

*** In this case carvacrol and/or thymol are applied as an etheric oil extracted from the above-mentioned plants: 3–5 wt. %

The following example is merely given as an illustration of the invention and should not be interpreted in a restrictive way.

Example 1

The following powder composition was applied:

$CaCO_3$: 25 wt. %

Magnesium stearate: 5 wt. %

Potato starch: 25 wt. %

Dextrose: 41 wt. %

Carvacrol and/or Thymol: 4 wt. %

In a farm 90 turkeys, suffering from both histomoniasis and rhinitis were treated with the above-defined composition in a dosis of 5 g/kg over 10 days. At the first day of the treatment only one turkey died. The others recreated quickly, and only some of them still had rhinitis.

For comparison purposes 90 turkeys of the same group as above, also suffering from both histomoniasis and rhinitis, were treated by the marketed product "Bayril". However, 20 turkeys died without showing sulfur-coloured feces before. At necropsy of four of these turkeys, they showed the typical picture of typhlohepatitis in different degrees of severity.

I claim:

1. A method of treating a malady which is diseases induced by hemoflagellates in poultry, comprising administering to poultry suffering therefrom, an effective amount of at least one member selected from the consisting of thymol and carvacrol, said amount being effective to treat said malady.

2. A method as claimed in claim 1, wherein said member is administered in a composition containing 1 to 10% by weight of said member.

3. A method as claimed in claim 1, wherein said member is administered in a composition containing 2 to 5% by weight of said member.

4. A method of preventing a malady which is diseases induced by hemoflagellates in poultry, comprising administering to poultry an effective amount of a member selected from the consisting of thymol and carvacrol, said amount being effective to prevent said malady.

5. A method as claimed in claim 4, wherein said member is administered in a composition containing 1 to 10% by weight of said member.

6. A method as claimed in claim 4, wherein said member is administered in a composition containing 2 to 5% by weight of said member.

* * * * *